US006387612B1

(12) United States Patent
Segall et al.

(10) Patent No.: US 6,387,612 B1
(45) Date of Patent: *May 14, 2002

(54) METHOD OF PREPARING A TERMINALLY HEAT STERILIZED PLASMA-LIKE SOLUTION

(75) Inventors: Paul E. Segall; Hal Sternberg; Harold D. Waitz; Judith M. Segall, all of Berkeley, CA (US)

(73) Assignee: BioTime, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/384,859

(22) Filed: Aug. 27, 1999

Related U.S. Application Data

(63) Continuation of application No. 08/896,824, filed on Jul. 18, 1997, which is a continuation of application No. 08/253,384, filed on Jun. 3, 1994, now Pat. No. 5,702,880, which is a continuation-in-part of application No. 08/133,527, filed on Oct. 7, 1993, now abandoned, which is a continuation-in-part of application No. 08/071,533, filed on Jun. 4, 1993, now Pat. No. 5,407,428.

(51) Int. Cl.$^7$ ............................ A01N 1/02; A61M 37/00
(52) U.S. Cl. ............................................ 435/1.2; 604/4
(58) Field of Search ........................... 435/1.1, 1.2, 1.3; 604/4

(56) References Cited

U.S. PATENT DOCUMENTS

| | | | |
|---|---|---|---|
| 3,937,821 A | 2/1976 | Irikura et al. | 424/180 |
| 3,949,098 A | 4/1976 | Bangert | 426/324 |
| 4,001,401 A | 1/1977 | Bonsen et al. | 424/177 |
| 4,061,736 A | 12/1977 | Morris et al. | 424/177 |
| 4,216,205 A | 8/1980 | Radowitz | 424/101 |
| 4,663,166 A | 5/1987 | Veech | 424/146 |
| 4,908,350 A | 3/1990 | Kramer et al. | 514/2 |
| 4,923,442 A | 5/1990 | Segall et al. | 604/52 |
| 4,927,806 A | 5/1990 | Kramer et al. | 514/2 |
| 5,082,831 A | 1/1992 | Leaf et al. | 514/56 |
| 5,084,377 A | 1/1992 | Rowan et al. | 435/1 |
| 5,120,719 A | 6/1992 | Iwamoto et al. | 514/54 |
| 5,130,230 A | 7/1992 | Segall et al. | 425/1 |
| RE34,077 E | 9/1992 | Segall et al. | 604/52 |
| 5,171,526 A | 12/1992 | Wong et al. | 422/28 |
| 5,374,624 A | 12/1994 | Segal | 514/21 |
| 5,407,428 A | 4/1995 | Segall et al. | 604/28 |
| 5,702,880 A | * 12/1997 | Segall et al. | 435/1.2 |

FOREIGN PATENT DOCUMENTS

| | | | |
|---|---|---|---|
| GB | 1 313 164 | * | 4/1970 |
| WO | 92/05693 | * | 4/1992 |

OTHER PUBLICATIONS

Klotz et al., "Clinical Pharmacokinetic Considerations in the Use of Plasma Expanders", Clinical Pharmacokinetics 12 : 123–135 (1987).*
Guyton's Textbook of Medical Physiology, Eighth Ed., W.B. Saunders Co., p. 277 (1991).*
Belzer, F.O. et al., (1985) "Combination Perfusion–Cold Storage for Optimum Cadaver Kidney Function and Utilization," *Transplantation* 39:118–121.
Bishop, M.C. and Ross, B.D., (1978) "Evaluation of Hypertonic Citrate Flushing Solution for Kidney Preservation Using the Isolated Perfused Rat Kidney," *Transplantation* 25:235–239.
Collins, G.M., 1969) "Hypothermic Kidney Storage," *Transplantation Proceedings* IX:1529–1534.

* cited by examiner

Primary Examiner—Sandra E. Saucier
(74) Attorney, Agent, or Firm—Bret E. Field; Bozicevic, Field & Francis

(57) ABSTRACT

Aqueous solutions comprising a polysaccharide oncotic agent, a physiologically compatible buffer, a simple hexose sugar, dissolved chloride salts of calcium, sodium and magnesium, and a dissolved organic salt of sodium are disclosed. The solutions are effective substitutes for blood and may be used to preserve the biological integrity of the organs of a mammalian donor organism as shown by superior anatomical integrity of cryopreserved organs and tissues of subjects perfused with the solution. The solutions may be used for maintaining a partially or substantially completely exsanguinated subject at normal temperatures and at temperatures substantially below those normally maintained by a mammal and may be used in conjunction with hypobaric environments to maintain such partially or completed exsanguinated subjects alive without infusing blood back into the subject.

5 Claims, No Drawings

METHOD OF PREPARING A TERMINALLY HEAT STERILIZED PLASMA-LIKE SOLUTION

CROSS-REFERENCES

This application is a continuation or application Ser. No. 08/896,824 filed Jul. 18, 1997; which application is a continuation of application Ser. No. 08/253,384 filed Jun. 3, 1994 and now issued as U.S. Pat. No. 5,702,880; which application is a continuation-in-part of application Ser. No. 08/133,527 filed Oct. 7, 1993 and now abandoned; which application is a continuation-in-part of application Ser. No. 08/071,533 filed Jun. 4, 1993 and now issued as U.S. Pat. No. 5,407,428; the disclosures of which applications are herein incorporated by reference.

FIELD OF THE INVENTION

The present invention relates generally to the field of aqueous solutions such as plasma-like solutions used to perfuse a living subject in need of perfusion and which act as effective substitutes for blood. The invention also relates to methods of preserving the biological integrity of the organs of a mammalian donor organism (as shown by superior anatomical integrity of cryopreserved organs and tissues of subjects perfused with the solution of the invention) and to methods of maintaining a partially or substantially completely exsanguinated subject at temperatures substantially below those normally maintained by a mammal.

BACKGROUND OF THE INVENTION

Two clinically applied preservation methods for organs are known: (1) initial perfusion for about 5 min with subsequent cold storage (2° C.), and (2) continuous perfusion using solutions containing albumin or plasma.

Many of the solutions used for initial perfusion with subsequent cold storage are based on the solutions of Collins et al. (1969) Lancet 2:1219 and Sacks et al. (1973) Lancet 1:1024. Ross et al. (1976) Transplantation 21:498 compared canine renal preservation following flushing and storage for 72 hours in various solutions. It was found that only kidneys preserved in a hypertonic citrate (HC) solution (comprising in part 80 mM $K^+$, 55 mM citrate, 400 mOsmol/kg, pH 7.1) survived after 72 hours. The Collins and Sacks solutions in part contained 115–126 mM $K^+$, 290–430 mOsmol/kg, pH 7.0–7.3. Wall et al. (1977) Transplantation 22:210 reports the hypothermic preservation of human livers for up to about 4 hours in a solution in part comprising 250 mg dextrose, and 15 mEq potassium phosphate. Bishop & Ross (1978) Transplantation 25:235 reported that renal function was preserved best in the HC solution of Ross et al. (1976) supra, rather than other available solutions. Fischer et al. (1985) Transplantation 39:122 found a new preservation solution for hypothermic ischemic storage (comprising in part 110 mM $Na^+$, 115 mM $K^+$, 400 mOsm/kg, solvent $D_2O$, 110 mM HEPES) to be superior to other solutions in clinical use, including Collins, Sacks, and HC.

Among the solutions used for continuous organ perfusion, Belzer et al. (1985) Transplantation 39:118 reported a newly developed solution which preserved renal function when kidneys were perfused for 48 hours and stored for 24 hours,(comprising in part 80 mM sodium gluconate, 22 mEq/l $K^+$, 128 mEq/l $Na^+$, 4.9 mM adenosine, 10 mM HEPES, 3.0 mM glutathione, 3.75 g % albumin, pH 7.45). Kallerhoff et al. (1985) Transplantation 39:485 examined the effect of temperature on pH of organs continuously perfused with two different solutions (Euro-Collins: 10 mM $Na^+$, 115 mM $K^+$, 198 mM glucose, 406 mOsm/L, pH 7.2 at 20° C.; HTK: 15 mM $Na^+$, 10 mM $K^+$, 2.0 mM tryptophan, 180 mM histidine, 30 mM mannitol, 310 mOsm/L, pH 7.3 at 8° C.). At incubation temperatures between 5° C.–35° C., HTK solution maintained pH at consistently higher values than Euro-Collins solution.

Klebanoff & Phillips (1969) Cryobiology 6:121 describe hypothermic asanguinqus perfusion of dogs perfused with buffered Ringer's lactate at 7.1 to 16° C. Segall et al. (U.S. Pat. No. 4,923,442) describe a blood substitute capable of maintaining a subject and its organs at temperatures below 20° C. having four different solutions—a base solution, a cardioplegia-inducing solution, a cardioplegia-maintaining solution, and a recovery solution. The base solution contains electrolytes in physiological concentration, a macromolecular oncotic agent, a conventional biological buffer effective at physiological pH, sugar, and $K^+$ ranging from 4–5 mEq. The cardioplegia-inducing solution had a $K^+$ concentration of 25–45 mEq; the cardioplegia-maintenance solution had a $K^+$ concentration of 15–45 mEq; and the recovery solution had a $K^+$ concentration of 6–10 mEq. Segall et al. (U.S. Pat. No. 5,130,230) further described the four-solution system, where the recovery solution contains 0–10 mEq $K^+$.

SUMMARY OF THE INVENTION

This invention features methods of using a single solution suitable to maintain a partially or substantially completely exsanguinated subject alive at normal temperatures or at temperatures substantially below those normally maintained by a mammal, generally less than 37–38° C. and greater than −2° C., comprising a sub- and/or physiological levels of $K^+$ and $Mg^{++}$; physiological $Na^+$, $Ca^{++}$, $Cl^-$; a macromolecular oncotic agent; an organic carboxylic acid or salt thereof; and a sugar.

The solution of the invention may be used as a plasma extender at normal body temperature. The solution of the invention is also useful to maintain the life or the biological integrity of a perfused subject and/or its organs during and after exposure to profound hypothermic conditions. The solution can also be used to maintain a euthermic subject in a pressurized environment with increased oxygen concentration up to 100% $O_2$ for time periods sufficient to permit adequate restoration of the subject's blood components.

The solution according to the invention may be used to perfuse and chill a mammalian subject to temperatures profoundly hypothermic to the subject's normal temperature. The solution can be used to maintain the subject in profound hypothermia for long periods of time, usually exceeding an hour, from which an intact subject can recover without apparent durable ill effects.

An important distinction of the solution of the present invention is that it does not require multiple solutions for it to be effectively administered to a subject for the purposes of blood substitution, or low temperature maintenance of a mammalian subject. The solution of the invention may be used at all phases of plasma extension or blood substitution.

Another important distinction of the solution of the present invention is the feature of a subphysiological amount of $K^+$ at all steps of administration. This requirement reduces the risk of hyperkalemia-induced heart sufficiency resulting in blood transfusion in primates and humans.

Another important distinction of the solution of the present invention is the absence of a conventional biological buffer. The absence of a conventional biological buffer in the solution confers the important medical advantage of allowing the solution to be terminally heat sterilized without degradation of solution components.

The solution of the present invention requires the presence of an organic carboxylic acid, salt, or short chain esters thereof. The organic carboxylic acid, salt or ester thereof is a component of the dynamic buffer system of the solution able to maintain a biologically appropriate pH range when used in a mammal.

The solution of the present invention requires the presence of a macromolecular oncotic agent sufficient to maintain physiological osmotic pressure. The macromolecular oncotic agent used in the solution of the present invention may be a protein(s) or starch(es).

An advantage of the solution is that it can be used in a mammalian subject during all phases of blood substitution from initial washout of the subject's blood through full substitution of all or substantially all circulating blood.

A feature of the invention is that it may be used to maintain a mammal without blood and also during reperfusion with blood.

DETAILED DESCRIPTION OF PREFERRED EMBODIMENTS

It must be noted that as used herein and in the appended claims, the singular forms "a," "an," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Red blood cells of primates contain high concentrations of potassium ion ($K^+$). When primate blood is stored (as is the case with virtually all blood obtained from blood banks), even low levels of lysis of the red blood cells generally result in high potassium ion concentrations. This is due to release of potassium ion from inside the lysed primate red blood cells into the plasma surrounding the cells. Accordingly, the blood will be hyperkalemic when infused. The increased potassium level can be diffused if blood is infused into patients with sufficient circulating blood since the high potassium ion concentration is diluted. However, the problem increases if primate blood is transfused into a maintenance solution of the type described in U.S. Pat. No. 4,924,442, which contains high concentrations of potassium. The potassium ion concentration in the transfused blood will not be diluted to safe levels. As a result, cardiac insufficiency may and frequently does occur. Hyperkalemia is also associated with tissue damage resulting from burns, accidents, surgery, chemotherapy, and other physical traumas. The prior art teaches that organ preservation at low temperatures requires the presence of high potassium ion concentrations for the maintenance of tissue integrity.

The solution according to the present invention contains a subphysiological amount of potassium. Thus, the solution allows for dilution of the potassium ion concentration in stored transfused blood. As a result, high concentrations of potassium ion and potential cardiac arrhythmias and cardiac insufficiency caused thereby can be more easily controlled. The solution containing a subphysiological amount of potassium is also useful for purposes of blood substitution and low temperature maintenance of a subject. By "subphysiological amount of potassium" is meant between 0–5 mEq/l $K^+$ (0–5 mM), preferably 2–3 mEq/l $K^+$ (2–3 mM).

The solution of the present invention comprises a mixture of materials which when placed in aqueous solution may be used to perfuse a subject in need thereof. While the materials may be provided as a dry mixture to which water is added prior to heat sterilization, the solution is preferably provided in the form of a sterile aqueous solution.

The solution of the present invention may be used as a single solution for all phases of procedures in which a subject's blood is removed and replaced or a subject is cooled. Such phases include hemodilution or plasma extension at normal body temperatures, blood replacement and exchange at hypothermic body temperatures, blood substitution at substantially hypothermic body temperatures, and subject warming. "Hypothermic body temperatures" are defined as 4–5° C. below normal body temperatures of 37–38° C. In other words, a hypothermic condition may be considered to start at body temperatures of about 32–35° C. "Substantially hypothermic body temperatures" are defined as body temperatures just below the freezing point (–2° C.) to about 10° C. Therefore, the term "hypothermic body temperature" or "hypothermia" as used herein encompasses body temperatures of about –2 to 3° C. to about 32–35° C.

The solution of the present invention does not include a conventional biological buffer. By "conventional buffer" is meant a compound which in solution, in vitro, maintains pH at a particular range. By "conventional biological buffer" is meant a compound which in a cell-free system maintains pH in the biological range of 7–8. Examples of conventional biological buffers include N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino) ethanesulfonic acid (TES), 3-[N-tris(Hydroxy-methyl)methylamino]-2-hydroxyethyl]-1-piperazinepropanesulfonic acid (EPPS), Tris[hydrolymethyl]-aminomethane (THAM), and Tris [Hydroxylmethyl]methyl aminomethane (TRIS). Conventional biological buffers function independently of normal biological processes, e.g., the conventional buffer is not metabolized in vivo, and are most potent in cell-free systems.

The solution of the present invention uses normal biological components to maintain in vivo biological pH, a concept termed a "dynamic buffering system". The dynamic buffering system concept rests on the discovery by the inventors that compounds with no intrinsic buffering capacity in the biological range, such as lactate, capable of being metabolized in vivo, act with other solution components to maintain a biologically appropriate pH in an animal, even at hypothermic temperatures and at essentially bloodless conditions. The dynamic buffering system of the present invention depends in part on oxygenation and removal of carbon dioxide ($CO_2$); and allows but does not, require additional bicarbonate ($NaHCO_3$). The dynamic buffer of the invention has no or substantially no ability to act as a buffer outside of a biological system, i.e., a dynamic buffer maintains pH in the biological range in vivo but not in a cell free environment. A component of the dynamic buffering system of the invention include a carboxylic acid, salt or ester thereof. What is meant by a carboxylic acid, salt or ester thereof is a compound having the general structural formula RCOOX, where R is an alkyl, alkenyl, or aryl, branched or straight chained, containing 1 to 30 carabons which carbons may be substituted, and preferably one of the carbon chains that compose the carbon chain of lactate, acetate, citrate, pyruvate, or other biological metabolites; and X is hydrogen or sodium or other biologically compatible ion substituent which can attach at the oxygen position, or is a short straight or branched chain alkyl containing 1–4 carbons, e.g., —$CH_3$, —$CH_2CH_3$.

As shown in Table 1, a typical conventional buffer solution (25 mM TRIS) that has an initial pH of about 7.7, and maintains a pH above 7.2 with the addition of up to 0.12 mls of a 1.25 M HCl solution. By contrast, the pH of HLB solution (initial pH 7.7) drops below 7.2 with the addition of about 0.01 ml of a 1.25 M HCl solution.

When the solution of the present invention is used as a blood substitute at hypothermic temperatures, medical grade sterile $NaHCO_3$ is added to the heat sterilized solution (HL solution). The solution containing $NaHCO_3$ is called HLB solution. The buffering capacity of HLB solution relative to a conventional biological buffer in a cell-free system is shown in Table 1. Under in vivo conditions with oxygenation, HLB solution is shown to maintain pH above 7.3 in temperatures ranging from 1.6–36.1° C. (Tables 2 and 3).

When the solution of the invention is used as a plasma extender at normal body temperatures, in vivo pH is maintained in the biological range without the addition of $NaHCO_3$.

The absence of a conventional biological buffer in the solution of the invention confers the important medical advantage of allowing the solution to be terminally heat sterilized. Generally, medical solutions are preferred to be terminally heat sterilized prior to use in a patient. The term "terminally heat sterilized" or "heat sterilized" as used herein referes to the process involving heating a solution to 120° C. for 15 minutes under pressure, i.e., maintaining heat and pressure conditions for a period of time sufficient to kill all or substantially all bacteria and inactivate all or substantially all viruses the solution. This procedure is normally performed in an autoclave, and is also known as "autoclaving". The purpose of heat sterilization is to kill possible infectious agents present in the solution. Infectious agents are known to tolerate temperatures up to 100° C. It is generally considered by the art that heating a solution under pressure to 120° C. for about 15 minutes is sufficient to insure sterility.

All transplant or blood substitute solutions of which the inventors are aware cannot tolerate terminal heat sterilization. It is known that heat sterilizing a solution having a pH above 7.0 results in substantial degradation of other solution components.

By contrast, the solution of the present invention is designed to be heat sterilizable with minimal degradation of other solution components, such as sugar. Solution HL is heat sterilized prior to use. When it is desirable to add $NaHCO_3$ to form HLB solution, $NaHCO_3$ is added as a commercially-available sterile 1 M solution to sterile HL solution. Generally, 5 mls of a 1 M $NaHCO_3$ solution is added per liter of HL solution to form 1 l of HLB solution. However, more $NaHCO_3$ may be added.

The HLB solution of the present invention, or its buffering organic acids and salts, may also be used to sustain cultured tissues and cells in vitro. The dynamic buffering system of the solution maintains cultured tissues and cells at the appropriate biological pH. We have shown that the addition of lactate and bicarbonate to cultured cells is sufficient to sustain normal cell growth and morphology.

The solution of the present invention includes an organic carboxylic acid or salt thereof. The term "organic carboxylic acid or salt thereof" includes any carboxylic acid or carboxylic acid derivative capable of being metabolized by the mammal. Examples of carboxylic acids and carboxylic acid salts suitable for use in the solution of the present invention include lactate and sodium lactate, citrate and sodium citrate, gluconate and sodium gluconate, pyruvate and sodium pyruvate, succinate and sodium succinate, and acetate and sodium acetate. In the following Examples describing the use of HLB solution, sodium lactate is used. When metabolized in vivo, lactate helps maintain bicarbonate levels, and thereby functions as a component of the dynamic buffering system of the solution to maintain an in vivo biological pH.

For purposes of the further description of the invention, the mixture according to the invention will be discussed as an aqueous solution. From the following description of the invention, it is expected that one ordinarily skilled in the art would be enabled to provide the mixture as a dry mixture and make the adjustments to amounts of sodium chloride and organic salt of sodium as necessary to accommodate the amounts of sodium chloride found in normal saline solution, which may be used as a diluent for the dry mixture according to the invention.

The amount of organic salts of sodium is calculated in a manner so as to consider the concentration of sodium ions present in the subject's blood as well as the sodium chloride concentration of any solution to which dry components are added. An amount is added so that the concentration of sodium ion obtained from the organic salt of sodium is sufficient to bring the concentration of sodium ion in the solution to a concentration about that of physiologically normal plasma. Therefore, when taking into account the amount or concentration of sodium ion obtained from the organic salt of sodium and sodium chloride, the concentration of sodium ion in the solution is about the concentration of sodium ion found in physiologically normal plasma.

The solution also includes a concentration of calcium, sodium and magnesium ion which is within the range of normal physiological concentrations of said ions in plasma. In general, the desired concentration of these ions is obtained from the dissolved chloride salts of calcium, sodium and magnesium and in the case of sodium from a dissolved organic salt of sodium which is also in solution.

The sodium ion concentration is preferably in a range from 70 mM to about 160 mM, and preferably in a range of about 130 to 150 mM.

The concentration of calcium ion is in a range of about 0.5 mM to 4.0 mM, and preferably in a range of about 2.0 mM to 2.5 mM.

The concentration of magnesium ion is in a range of 0 to 10 mM, and preferably in a range of about 0.3 mM to 0.45 mM. It is important not to include excessive amounts of magnesium ion in the solution according to the invention because high magnesium ion concentrations negatively affect the strength of cardiac contractile activity. In a preferred embodiment of the invention, the solution contains subphysiological amounts of $Mg^{++}$.

The concentration of chloride ion is in the range of 70 mM to 160 mM, preferably in the range of 110–125 mM $Cl^-$.

The solution also includes an amount of simple hexose sugar such as glucose, fructose and galactose, of which glucose is preferred. In the preferred embodiment of the invention nutritive hexose sugars are used and a mixture of sugars can be used in general, the concentration of sugar is in a range between 2 mM and 10 mM with concentration of glucose of 5 mM being preferred. At times, it is desirable to increase the concentration of hexose sugar in order to lower fluid retention in the tissues of a subject. Thus the range of hexose sugar may be expanded up to about 50 mM if necessary to prevent or limit edema in the subject under treatment.

The oncotic agent is comprised of molecules whose size is sufficient to prevent their loss from the circulation by traversing the fenestrations of the capillary bed into the interstitial spaces of the tissues of the body. As a group, oncotic agents are exemplified by blood plasma expanders.

Human serum albumin is a blood plasma protein used to expand plasma volume. Also known are polysaccharides, generally characterized as glucan polymers which are used as blood plasma expanders. In general, it is preferred that the polysaccharide is non-antigenic.

Hetastarch, which is a tradename for hydroxyethyl starch, is a glucan polymer which can act as an artificial colloid when dissolved in water. Hydroxyethyl starch is derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.7 which means hydroxyethyl starch has 7 hydroxyethyl groups for every 10 glucose units. The average molecular weight of hydroxyethyl starch is 480,000 with a range of 400,000 to 550,000 and with 80% of the polymers falling in the range of 30,000 to 2,400,000. Hydroxyethyl groups are attached by ether linkage primarily at C2 of the glucose unit and to a lesser extent the C3 and C6 position. The glucose units are joined primarily in alpha (1 - - - 4) linkage with occasional 1 - - - 6 branches. The colloid properties of a 6% solution (wt/wt) of Hydroxyethyl starch approximates that of human serum albumin, with approximately 33% of a 500 ml intravenous dose eliminated in the urine after 24 hours. Approximately 10% of the dose remains circulating after 1 week. As used herein Hydroxyethyl starch is referred to as high molecular weight hydroxyethyl starch.

Pentastarch is another glucan polymer which can act as an artificial colloid when dissolved in water. Pentastarch is also derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.45 which means pentastarch has 45 hydroxyethyl groups for every 100 glucose units. The average molecular weight of pentastarch is approximately 264,000 with a range of 150,000 to 350,000 and with 80% of the polymers falling in the range of 10,000 to 2,000,000. Hydroxyethyl groups are attached by ether linkage primarily at C2 of the glucose unit and to a lesser extent the C3 and C6 position. The glucose units are joined primarily in alpha (1 - - - 4) linkage with occasional 1 - - - 6 branches. As used herein pentastarch is referred to as low molecular weight hydroxyethyl starch.

Hetastarch (McGaw, Inc.) is an artificial colloid derived from a waxy starch composed almost entirely of amylopectin with hydroxyethyl ether groups introduced into the alpha (1 - - - 4) linked glucose units. The colloid properties of a 6% solution (wt/wt) of Hetastarch approximates that of human serum albumin. Other polysaccharide derivatives may be suitable as oncotic agents in the solutions according to the invention including hydroxymethyl alpha (1 - - - 4) or (1 - - -6) polymers. Cyclodextrins are suitable oncotic agents.

D-glucose polymers may be used. For example, dextran, which is D-glucose linked predominantly in alpha (1 - - - -6) linkage, may be used as the oncotic agent in the solution of the invention. Polysaccharides such as dextran in a molecular weight range of 30,000 to 50,000 daltons (D) are preferred. Most preferred is Dextran 40 having a molecular weight of about 40,000 D.

High molecular weight polysaccharides, such as Dextran 70, having a molecular weight of about 70,000 D are generally less preferred because they increase the viscosity of the colloidal solution, thereby impairing high flow rates. However, for some uses, high molecular weight dextran solutions are preferred in that they are more effective in preventing tissue swelling due to their lower rates of leakage from capillaries. Thus, such high molecular weight dextran solutions are particularly useful in the treatment of cerebral ischemia at hyperbaric oxygen tensions and in effectively managing cerebral oedema. In such circumstances, it may be desirable to use higher molecular weight polysaccharide such as dextran in a molecular weight range of 50,000 to 70,000 D.

When Dextran 40 is used in the solutions according to the invention, about 8t Dextran 40 (wt/wt) or about 80 grams (g) per liter (l) of water is used. Molarity of the blood substitute according to the invention will be in a range of about 290 to 330 milliMolar with a molarity of about 300 being preferred. Most preferred is a final molarity of about 298 mM.

The concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

The solution may be used as a circulating solution in conjunction with oxygen or hyperbaric oxygen at normal body temperatures, or with or without hyperbaric oxygen in subjects during procedures. The solution may also be used as a circulating solution in subjects during procedures when the subject's body temperature is reduced significantly below the subject's normal temperature. When warm-blooded subjects are exposed to low temperature conditions during surgical procedures and in cadaver organ donation at low temperature, it is generally desirable to replace the subject's blood with the cold circulating solution of the invention, or the solution circulated for a time, designed to perfuse and maintain the subject and its organs intact during the procedure.

The solution of the present invention may be administered intravenously or intraarterially to a euthermic subject which is placed in a pressurized atmosphere of increased oxygen concentration up to 100% oxygen or to such a subject undergoing a procedure during which the subject's body temperature is reduced significantly below the subject's normal temperature whether or not hyperbaric oxygen is used. While the solution is being administered to and circulated through the subject, various agents such as cardioplegic agents may be administered either directly into the subject's circulatory system, administered directly to the subject's myocardium, or added to the circulating solution of the present invention. These components are added to achieve desired physiological effects such as maintaining regular cardiac contractile activity, stopping cardiac fibrillation or completely inhibiting contractile activity of the myocardium or heart muscle.

Cardioplegic agents are materials that cause myocardial contraction to cease and include anesthetics such as lidocaine, procaine and novocaine and monovalent cations such as potassium ion in concentrations sufficient to achieve myocardial contractile inhibition. Concentrations of potassium ion sufficient to achieve this effect are generally in excess of 15 mM.

During revival of a subject (after a period of subnormal temperature or cryogenic maintenance using the solution according to the invention to maintain the subject) the subject may be reinfused with a mixture of the solution according to the invention along with blood retained from the subject or obtained from blood donors. As the subject is warmed, whole blood is infused until the subject achieves an acceptable hematocrit, generally exceeding hematocrits of about 30%. When an acceptable hematocrit is achieved, perfusion is discontinued and the subject is revived after closure of surgical wounds using conventional procedures.

In general, the solution according to the invention is administered using an intravenous line (when the subject is at normal temperature) or to a chilled subject using a pumped circulating device such as a centrifugal pump, roller pump, peristaltic pump or other known and available circulatory pump. The circulating device is connected to the subject via cannulae inserted surgically into appropriate veins and arteries. When the solution is administered to a chilled subject, it is generally administered via an arterial cannula and removed from the subject via a venous cannula and discarded or stored.

The solution may be used in a variety of surgical settings and procedures. It may be useful in delicate neurosurgery where clear surgical fields are imperative and reduced central nervous system activity may be desirable and achieved by performing the procedure on a patient whose core temperature and/or cerebral temperature has been substantially reduced.

The solution may be used to maintain a subject (which has lost a significant amount of blood, e.g. 20% to 98% of its blood) at normal body temperatures in a pressurized environment at increased oxygen concentration above atmospheric oxygen tension up to 100% oxygen. The subject is maintained in a high oxygen concentration until enough blood components can be synthesized by the subject to support life at atmospheric pressure and oxygen concentration. The solution according to the invention may be used to maintain a subject at temperatures lower than normal body temperature and at a reduced rate of metabolism after traumatic life threatening injury until appropriate supportive or corrective surgical procedures can be performed. In addition the solution may be used to maintain a patient having a rare blood or tissue type until an appropriate matching donor can be found and replacement blood units or other organ can be obtained.

Surprisingly it has been discovered that it is possible to replace substantially all of a mammalian subject's circulating blood with the solution according to the invention and to maintain the subject alive a without reinfusing blood into the subject. Substantially all of a mammalian subject's circulating blood is considered to be replaced when the subject's hematocrit drops below 10%. Hematocrit may be lower than 10% if $O_2$ is provided to the subject, or substantially lower than 10% in a hyperbaric $O_2$ chamber. The solution according to the invention can of course be used to maintain a subject having a hematocrit in excess of 10%.

The procedure for replacing substantially all of a mammalian subject's circulating blood may be carried out with the mammalian subject's body temperature being maintained at its substantially normal temperature. In addition the procedure may be carried out with cooling of the subject and reduction of the mammalian subject's body temperature below that of its normal temperature. Cooling may be accomplished by chilling the subject in an ice bath, ice-salt slurry, or cooling blanket. The subject may be further cooled by chilling the solution according to the invention prior to perfusing the subject with the solution.

In the procedure according to the invention for replacing substantially all of a mammalian subject's circulating blood, it is preferred that the subject is chilled and perfused with the solution, using an arterial catheter to deliver the solution to the subject's circulatory system and a venous catheter to remove blood and the perfusate from the subject. Substantially all of the subject's circulating blood is removed in this manner as determined by measurement of the hematocrit of the effluent from the venous catheter. When substantially all of the subject's circulating blood is removed, perfusion is stopped.

In addition, the procedure for replacing substantially all of the subject's blood may be carried out with the aid of hyperbaric $O_2$. The subject is placed in a hyperbaric chamber pressurized with oxygen at concentrations exceeding 20%, preferably 100% oxygen. The pressure of the hyperbaric chamber is maintained during most of the procedure in a range between 0.5 pounds per square inch over atmospheric pressure to pressures up to about twice atmospheric pressure. In one embodiment, the procedure is performed with the subject in a hyperbaric chamber at hyperbaric pressures of about 0.07 to about 2 atmospheres over ambient pressure (0.5–30 pounds per square inch [psi]) with 100% oxygen. If necessary, the pressure of the hyperbaric chamber may be reduced to atmospheric pressure during wound closure. The subject is subsequently maintained at hyperbaric pressure at high oxygen concentration. The pressure is gradually reduced to a lower pressure but one still hyperbaric. Preferably the pressure is maintained below 10 psi to about 5 psi for a number of hours to several days. Subsequently, the pressure is again gradually lowered below 1 psi and preferably to about 0.5 psi and is maintained at this pressure for an additional period of time up to a day or more.

The solution may also be used to maintain the physiological integrity of an organ donor subject immediately after the occurrence of brain death. The subject can be chilled, the subject's blood removed and replaced with a circulating solution maintained below 37° C., or while circulating cold solution according to the invention. Through this use of the solution, ischemia of vital organs can be minimized. By circulating cold solution according to the invention through the subject's circulatory system at low temperature with or without placing the subject in a hyperbaric oxygen chamber, vital organs can be maintained for longer periods of time, thus maximizing the number of organs that can be effectively used from one donor for potential transplant recipients.

In another aspect of the invention, it has been discovered that by using certain adducts, particularly propanediol and high concentration glucose to augment the solution, it may be possible to reduce the temperature of donor organs, and in particular donor hearts, below the freezing point of water (0° C.) and recover them from freezing in a useful state, i.e. a state capable of maintaining coordinated cardiac contraction. Furthermore by using the solution according to the invention with such adducts, it has been possible to reduce the temperature of intact mammalian donor subjects below the freezing point of water (0° C.) and restore them from freezing in a state capable of maintaining coordinated cardiac contraction. Other organ systems are also believed to be maintained with a high degree of biological integrity, i.e. in a physiological state capable of maintaining life.

The adducts to the solution include low molecular weight aliphatic polyalcohols. Diols, exemplified by ethylenediol, propanediol, and butanediol are preferred. Of these diols propanediol is particularly preferred. Other polyalcohols that may be suitable as adducts for low temperature, sub-zero 0° C. preservation of organ and organ donor subjects are low molecular weight polyethylene glycol. It is preferred in this aspect of the invention that the adduct is added to the solution to a final concentration in a range between about 0.2 Molar to 1 Molar. With respect to propanediol, in particular a n range of 0.2M to 0.6M is preferred. A concentration of about 0.4M propanediol is most preferred. 1,2 propanediol is preferred as the adduct to the solution used for low temperature organ and donor preservation according to the invention, although 1,3 propanediol may be used.

The glucose concentration in the solution useful for sub-zero °C. preservation of organ and organ donor subjects ranges between about 0.6M to about 1.4M. A concentration of about 1M glucose is preferred.

Another adduct that is useful in the solution for low temperature and sub-zero 0° C. preservation of organ and organ donor tissues is trimethylamine oxide (TMAO). TMAO may be added to the solution described immediately above to a final concentration in a range between 0.2M and 7M. The solution including TMAO when perfused into a subject leads to improved biological integrity of the subject's tissues as evidenced by superior anatomical preservation of the tissues.

The following Examples are intended to illustrate the invention and its use, and are not intended by the inventors to be limiting of the invention.

EXAMPLES

The following example is put forth so as to provide those of ordinary skill in the art with a complete disclosure and description of how to carry out the synthesis of the invention and is not intended to limit the scope of what the inventors regard as their invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

EXAMPLE 1

Solution Preparation.

Preparation of 10 L of Solution A.

Into an appropriate container, add 80 g/L (or 800 g for 10 liters) of pyrogen-free Dextran 40 (Pharmachem or Pharmacia). Add deionized water, bringing the volume up to 6–9 liters. Dissolve the Dextran 40 completely by shaking. The following components may be added in any order, dissolving each completely before the addition of the next. The following reagents may be obtained from chemical supply houses; in this example the listed reagents were obtained from Sigma: NaCl (5.2 g/L), $CaCl_2$ (0.29 g/L), $MgCl_2$ (0.40 g/L), glucose (0.9 g/L), Tris (3.03 g/L), and sodium gluconate (6.54 g/L).

Next, the solution is brought to pH 7.80 at room temperature by the dropwise addition of 0.25M HCl while shaking and monitoring with a pH meter. The solution is then brought to its final desired volume (i.e. 10 liters) by the addition of more deionized water.

Finally, the solution is pumped through a 0.2 μ filter (Gelman, Whatman, or ideally Pall filter units can be used) into sterile containers or bags. The bottled and capped solution is stored on ice until used.

The solution may then be prepared as a sterile dry powder in containers suitable for preparation of sterile IV solutions after freeze drying under appropriate conditions.

Preparation of Solution HL.

To prepare 50 liters of solution HL (BioTime Hextend™-lactate), 3.0 kg of high molecular weight Hetastarch (HES) is added to 25 liters of water. Sufficient NaCl is added to bring the final NaCl concentration to 6.72 g/l. The solution is stirred until both the HES and NaCl are dissolved. The solution may be heated to 50° C. if necessary. The total volume is brought to 45 liters and the following components are added and mixed until completely dissolved: $CaCl_2.2H_2O$ 18.5 g; $MgCl_2.6H_2O$ 4.5 g; KCl 11.0 g; glucose 45.0 g; and sodium lactate 4.03 ml/liter of a 60% (wt/wt) solution. The solution is brought up to a volume of 50 liters. The solution is filtered to remove undissolved material and placed in autoclavable containers and heated in an autoclave to a temperature of 120° C. for 15 minutes.

Solution HLB.

To each heat sterilized liter or HL solution is added 5 ml of a sterile 1 M solution of $NaHCO_3$, medical grade, forming HLB solution (BioTime Hextend™-lactate-bicarbonate).

Solution L.

Solution L is prepared as described or HL solution above without the addition of Hetastarch (HES).

EXAMPLE 2

Hamster Revived After 1 hour of Ice-cold Blood-substitution.

A 41 g female hamster (*Mesocricetus auratus*), approximately 1 month old, was injected i.m. with 0.04 ml of Vetalar, a 100 mg/ml solution of the anesthetic ketamine. The animal was packed in crushed ice and chilled until its rectal temperature was 10° C. The animal was removed from the crushed ice and placed ventral side up on a custom-designed stage positioned so that specific portions of the animal could be observed through a stereo-microscope during surgery. Its limbs were secured, and the animal was instrumented with EKG leads and a rectal telethermometer probe.

An incision was made in the right groin region, and the right femoral vein, and then the right femoral artery, were cannulated using specially designed micro-cannulas filled with solution A. After cannulation, 0.02 ml of heparin (1000 U/ml) in solution A was injected into ran the animal through the venous cannula, which was then capped.

After the right femoral arterial cannulation, the cannula was connected to a luer-tipped segment of sterile plastic tubing which was connected to a stopcock mounted on the surgical stage. The stopcock was connected to another tubing segment which was in turn connected to a wider, thicker, and more compliant tubing segment passed through the head of a roller pump. The end of this wider tubing segment contained a tube for drawing up fluid from a reservoir. This tube for drawing up fluid from a reservoir termed a "pick-up" herein was fashioned from the luer end of an 18 gauge hypodermic needle. This "pick-up" was covered with blood filter material which was secured by a small rubber "O" ring. The "pick-up" was inserted into a reservoir of solution A contained by a centrifuge tube immersed in crushed ice. 01.06 ml of 1M KCl was added to the solution (15 ml), yielding a molar concentration of about 4mM KCl. The line was closed using the stopcock to prevent back-bleeding into the arterial cannula.

The hamster was surrounded with crushed ice, and chilled to 4° C. Then 0.2 ml of 1M KCl was injected into the stopcock, which was opened to allow the injected solution to flow into the line connecting to the arterial cannula, and from there, into the animal's femoral artery. The hamster's heart arrested. The animal was allowed to cool further, and was perfused through the arterial cannula with 8 ml of solution A 4 mM KCl. Effluent, containing most of the hamster's blood, was collected from the venous cannula. After the hematocrit dropped below 5, the roller pump was turned off for 67 minutes.

The hamster was then perfused through the arterial cannula with 8 ml of solution A without KCl, followed by 8 ml of heparinized blood taken from other hamsters by cardiac puncture. An equal amount of effluent was collected from the venous cannula. After the hematocrit exceeded 40%, perfusion with whole blood was ended, and the cannulas removed.

The hamster was warmed with a desk lamp, until it became reactive to stimuli. The cannulas were removed, open blood vessels ligated, and incisions closed.

Further rewarming continued. The animal fully recovered, and continued to live for weeks following the experiment.

EXAMPLE 3
Cardiac Preservation After Sub-zero Storage.

A fasted (overnight) female hamster, 40 grams, was injected, i.m., with 0.02 ml of Ketamine anesthetic (100 mg/ml). The hamster was immersed in crushed ice until its body temperature lowered to +14° C. It was then placed on a surgical stage and instrumented with EKG leads and a rectal temperature probe. The carotid artery and jugular vein were exposed surgically while the animals body temperature was maintained between 10–14° C. and cannulas were inserted into the artery and vein. The arterial cannula was attached to tubing connected to a peristaltic pump. The tubing was filled with solution A, containing in addition 20 mM KCl. The venous cannula was capped until the animal's body temperature was lowered to 5° C. using crushed ice and a temperature-controlled stage set at –1.0° C.

The animal stopped breathing on its own when its body temperature fell below 10° C. Respiration with 100% $O_2$ was initiated. At 5° C., the venous cannula cap was removed and 3.5 ml of solution A was pumped into the artery at a flow rate of about 0.3 ml/minute. Afterwards, 4.5 ml of a cryoprotective solution composed of solution A and in addition 4 mM KCl, 1.0M glucose, 4t propanediol (i.e. 1.8 g glucose+ 0.4 g propanediol per 10 ml solution) was infused. During perfusion, the venous effluent was collected. The animal's temperature was lowered gradually to 0° C. during perfusion. Respiration was discontinued 5 minutes following the onset of perfusion. At this time, more than 30% of the subject's blood volume had been removed. The heart continued beating until it eventually stopped. Following perfusion with the cryoprotective solution described in the preceding paragraph, the animal was placed in a sub-0° C. NaCl slush (0.6M) solution which was placed in a freezer overnight.

The freezer temperature was kept at an average of –5° C. Fifteen minutes after the animal was placed in the freezer, its rectal temperature lowered from 0 to –1.0° C. The animal's rectal temperature 12 hours later was –2.5° C. The animal was then warmed to a temperature of about 2.5° C. in a Quasar commercial kitchen microwave oven using 7 second pulses with the setting on warm. The pulses were generated 1 minute apart. Eighteen pulses were needed to thaw the animal.

The animal was again placed on the surgical stage and instrumented with EKG leads and a rectal telethermometer probe. Three and one half ml of solution A was perfused into the carotid artery at a flow rate of approximately 0.2 ml/in. The animal's body temperature was maintained below 5° C. The hamster was then perfused with whole blood, and gradually warmed.

After 2 ml of blood had been infused, and the animal's temperature had climbed to 13° C., rhythmic EKG signals were detected. With continued perfusion and warming, the amplitude of the signals became greater, and they increased in frequency. After 5.5 ml of blood had been infused, and the animal's temperature had reached 25° C., the chest of the animal was opened and its heart was observed to beat continuously.

EXAMPLE 4
Synthetic Solution Substitutes for Blood In A Hyerbaric Chamber.

A 40 g hamster, previously fasted overnight, was injected with 0.03 ml Ketamine (100 mg/ml) i.m. The hamster was placed in crushed ice, until its body temperature fell below 15° C. The hamster was removed from crushed ice, and placed ventral side up on a temperature-controlled stage positioned for microsurgery below a stereo-microscope. The hamster's temperature was maintained between 12–15° C.

Following an incision in the right groin area, the right femoral vein and artery were exposed. The femoral vein was cannulated, 0.1 ml of heparin (1000 u/ml) was injected, and the cannula was capped to prevent bleeding.

The right femoral artery was then cannulated, and the cannula was briefly attached to tubing filled with solution A. The tubing was threaded through the head of a peristaltic pump. A small volume of the solution (approximately 0.3 ml) was infused to keep the arterial cannula void of blood. Both the venous and arterial cannulas were secured to the animal with surgical suture.

The arterial cannula was capped and the animal was moved onto the stage in a hyperbaric oxygen (HBO) chamber. A temperature probe was inserted into the rectum.

The arterial cannula was attached to tubing which passed through a peristaltic pump and into a reservoir. The tubing and reservoir were filled with solution A containing 4 mM KCl.

The cap was removed from the venous cannula, and the HBO chamber was closed and pressurized. The peristaltic pump was turned on, and the animal perfused with solution, which replaced most of its blood. This blood was allowed to drain from the animal as a venous effluent. The final chamber pressure was 1.5 atm over ambient pressure, which was kept constant. The flow rate of solution into the animal was about 0.3 ml/min. The hamster was maintained between 14–16° C. using the temperature-controlled stage on which the hamster was positioned in the HBO chamber.

Cardiac activity and breathing were maintained throughout this period during the perfusion. After 15 ml of solution A containing in addition 4 mM KCl was perfused into the hamster replacing the blood, the chamber was gradually depressurized.

The chamber was then opened, and a hematocrit sample was taken. The hematocrit was 5%. The venous and arterial cannulas were capped and the chamber closed and pressurized to 1.5 atm over ambient pressure.

The animal continued to breathe on its own in the chamber for 4 hours after the removal of its blood. After this time, the chamber was depressurized gradually. Concomitantly, the animal was cooled to 12° C. The chamber was opened, and the animal was moved to another surgical stage. Ice was placed on the animal, and whole blood was perfused into the animal at a flow rate of 0.2 ml/min, as solution was allowed to drain as venous effluent.

After 1 ml of blood was infused, the ice was removed. The hamster's body temperature was at 4° C. The animal was then permitted to warm gradually as the hematocrit was raised by continuous blood infusion.

Artificial respiration was initiated after 1 ml of blood was put back in. The animal's heart never stopped beating rhythmically. At 21° C., the animal was breathing steadily on its own. Artificial respiration was discontinued and warming and blood infusion continued until the animal's temperature reached 25° C. The hematocrit was measured to be 40%. Perfusion was discontinued, the cannulas removed, blood vessels ligated and surgical incisions closed.

One hour following the procedure, the animal was very active and alert. Four hours after the experiment, the animal was eating and drinking. At 24 hours after the completion of the above-described procedure, it appeared completely normal with respect to posture and behavior, and continued to live for weeks after the experiment.

EXAMPLE 5

Ice-Cold Blood Substitution of a Hamster.

A 46 g hamster, approx. 1 month old, was injected i.m. with 0.02 ml Vetalar, a 100 mg/ml solution of ketamine. The animal was surrounded by crushed ice until its rectal temperature was about 12° C. The animal was then removed from the crushed ice and placed ventral side up on an operating stage designed to keep the animal cold, which is under a stereo-microscope. Its limbs were secured, and the animal was instrumented with EKC leads and a rectal telethermometer probe.

An incision was made in the right groin region. A cannula was placed in the right femoral vein, and 0.02 ml of heparin solution (250 U/ml) was injected into the animal through the cannula which was then capped. Then the right femoral artery was cannulated. The cannula was connected to a luer-tipped segment of plastic tubing, and the tubing was passed through a peristaltic roller pump and into a reservoir containing solution A containing 0.05 M glucose. At the end of the tubing was inserted an 18 G hypodermic needle to which a mesh blood filter material was secured at the hub by a rubber "O" ring. The pump was turned on, and fluid in the reservoir was pumped through the tubing into the femoral artery of the animal. When the animal's temperature fell below 9° C., ventilation (at 20 breaths/minute) was initiated using 100% oxygen. The animal was cooled further to a rectal temperature of 4° C., and 0.1 ml of 0.2M KCl was injected into the 24 G angiocath which was inserted in the femoral vein. This injection arrested the heart, and EKG signals ceased. The pump was turned on, and solution A was perfused into the artery at approximately 0.2 ml/min while venous effluent was collected. During the perfusion the animal's temperature dropped to near 1° C. After 4 ml of solution was perfused into the animal, the pump was turned off and the animal was kept surrounded by crushed ice in circulatory arrest for 2 hours. Then the animal was perfused with approximately 7 ml of whole blood (which was collected from other hamster blood donors) while the animal was gradually warmed using a desklamp. During the perfusion venous effluent was collected. The same volume pumped into the artery is collected as venous effluent. At 10° C., after the animal remained in cardiac arrest for 3 hours and 11 minutes, heart beats were first observed upon monitoring EKG signals. Ventilation (6 breaths/ minute) of the animal was then initiated using 100% oxygen. As the animal was further warmed and heart beats became stronger and faster, this rate was increased to about 15 breaths/minute. When the animal's temperature was above 28° C. the animal began to breathe on its own and became responsive.

Perfusion was discontinued (the hematocrit reading 44%) and cannulas were removed and surgical wounds closed. This hamster remained alive in apparently normal health for many weeks after the experiment.

EXAMPLE 6

Recovery of Heart Beat in an Ice-Cold Hamster.

A fasted (overnight) female hamster, 45 grams, was injected i.m. with 0.03 ml ketamine anesthetic (100 mg/ml). The hamster was immersed in crushed ice until its body temperature lowered to about 14° C. The animal was then placed on a surgical platform and instrumented is with EKG leads and a rectal temperature probe. The carotid artery and jugular vein were exposed surgically using a stereo microscope. The animal's body temperature was maintained between 10–14° C. Cannulas were inserted into the carotid artery and jugular vein. The arterial cannula was connected to tubing which passed through a peristaltic pump into a reservoir containing cryoprotective solution composed of solution A containing, in addition, 11 mM KCl, 1.0M glucose and 4% propanediol. The venous cannula was initially capped until the animal's body temperature was lowered to 5° C. using crushed ice and a temperature regulated platform set near –1.0° C.

The animal stopped breathing on its own as the body temperature fell below 10° C. At this time the animal was ventilated at about 15 breaths per minute with 100% oxygen. When the animal's temperature fell to 5° C., the venous cap was removed and the pump was turned on at a flow rate of about 0.20 ml/minute. The animal's heart stopped beating 21 minutes later, and ventilation was discontinued 5 minutes after the onset of perfusion. During the perfusion blood was collected as venous effluent. Approximately 4 ml of the cryoprotective solution A was infused into the animal. Then the animal was surrounded by a salt-ice slurry whose temperature was –2.0° C. The container that held the slurry and animal was placed inside a temperature bath set at –5.0° C. The animal's rectal temperature gradually lowered to –3.4° C. in the morning (18 hours after the animal was put in the cooling bath). The container was removed from the cooling bath. The slurry was frozen solid. It was melted using ice-cold water. Upon removing the "slurry" the animal felt frozen. The animal was then placed in a kitchen microwave oven. The oven was set on warm for 7 seconds. The animal was exposed to about 20, 7 second heating cycles over a 20 minute period. This thawed the animal and raised its rectal temperature to about 2° C.

The animal was again placed on the surgical platform, and the animal was infused into the carotid artery with solution A. The cryoprotective solution was collected as venous effluent. About 3 ml of solution A was perfused into the animal at a flow rate of 0.15 ml/minute. Blood which was collected from hamster blood donors was then perfused in at the same flow rate. After 2 ml of blood was perfused into the artery of the hamster, the hamster was warmed slowly using a desk lamp. As blood perfusion and warming continued, the animal's temperature rose above 15° C. and strong rhythmic EKG signals were recorded. Upon surgical thoracotomy actual heartbeats could be observed.

EXAMPLE 7

Synthetic Solutions as a Substitute for Blood in a Hyperbaric Oxygen Chamber.

A 43 gram female hamster (fasted overnight) was injected, i.m., with 0.02 ml of ketamine (100 mg/ml). The hamster was placed in crushed ice until its body temperature fell to about 14° C. The hamster was then placed ventral side up on a temperature-controlled stage positioned for microsurgery below a stereo-microscope. The hamster's temperature was maintained between 12–15° C. Following an incision in the right groin area, the right femoral vein and artery were exposed. The femoral vein was cannulated, 0.1 ml of heparin (250 u/ml) was injected, and the cannula was capped to prevent bleeding. The right femoral artery was then cannulated, and the cannula was attached to tubing passed through a peristaltic pump and into a reservoir filled with solution A. A small volume of the solution (i.e. 0.2 ml) was infused to keep the arterial line void of blood. Both the venous and arterial cannulas are secured to the animal. The arterial cannula was capped, and the animal was transferred onto the temperature-regulated stage of a hyperbaric oxygen (HBO) chamber. The animal's temperature measured rectally was maintained between 13–18° C. The purpose of maintaining the hamster in that temperature range was to keep the animal's activity low while ensuring the animal was breathing on its own and reflexively responsive to stimuli.

The arterial cannula was connected to tubing that passed outside the chamber through a peristaltic pump and into a reservoir (inside the chamber) which contained solution A and 2.5 mM KCl. The cap was removed from the venous cannula, and the pump was turned on at a flow rate of about 0.2 ml/min. As the solution was perfused into the animal, venous effluent (blood) was collected. The chamber was quickly closed and gradually pressurized to 20–24 psi (100% oxygen). After about 1 hour of perfusion under pressure the chamber was gradually depressurized over a period of about 1 hour. Then perfusion was discontinued. A total of about 13 ml of solution was perfused into the animal. The cannulas were capped after a sample of venous effluent was taken to determine the hematocrit. The animal was placed again on a surgical platform, and the cannulas were pulled out and wounds tied. The animal showed some very minimal reflex activity during this time although the animal had little blood and was breathing room air. The animal was quickly placed in a box inside the chamber which was pressurized gradually to about 20 psi. In the chamber was placed food and water for the hamster. A heat lamp was used to warm the chamber and the animal. The pressure in the chamber was gradually lowered (over a 1 hour period) to 5 psi. The animal's activity increased over the one hour period until it became quite active. The animal was maintained in the chamber for about 16 hours at 5 psi. The pressure was then gradually lowered to 0.5 psi (100% oxygen) and maintained at that pressure 24 hours. Then the animal was taken out of the chamber and was placed in a normal cage. The animal continued to appear completely normal many weeks following the experiment.

EXAMPLE 8

Use of Solution A Augmented with Potassium Chloride to Blood Substitute Primates In this example an 8 kg. juvenile male baboon of the species *Papio anubis* was injected i.m. with 60 mg of ketamine. A 22 gauge×1-¼ in. catheter was inserted in the right cephalic vein, and 3 ml of 2.5% pentothal was injected i.v. The animal was then fitted with an endotracheal tube, placed on a surgical table, and ventilated with a 0.7–2.5% mixture of Flether in 100% $O_2$, titrated to the animal's activity. The eyes were coated with lacrylube for protection.

The ventilator was set at 18 breaths per minute (bpm), its stroke volume was 240 ml, and the inspiratory/expiratory ratio was 37%. Airway pressure was maintained at approximately 10 mm Hg, and the volume delivered with each respiration was checked by examining the airway pressure trace on a CRT or strip-chart recorder. Airway pressure was monitored on-line by computer.

The animal was shaved, and Ringer's lactate drip was initiated i.v. at a flow rate of 1–3 ml/minute with the rate titrated to the animal's arterial blood pressure. Terramycin was administered.

The extracorporeal circuit consisted of a blood oxygenator, blood reservoir and pump and was constructed with a secondary in-line heat exchanger added as close to the animal as possible. It was further equipped with an external ice water reservoir. The ice-water reservoir had a pump to supply the oxygenator's built-in heat exchanger, as well as the secondary heat exchanger with circulating ice water. All tubing in contact with blood or blood substitute was sterile. The oxygenator reservoir and circuit was filled with 2 liters of solution A.

KCl (4 ml of 2.0 M) was added to the 2 liters of solution A in an oxygenator reservoir and bypass circuit, yielding a KCl concentration of 4 mM. A 5F NIH catheter for monitoring arterial pressure was introduced into the left brachial artery. To it was attached a 3-way stop-cock (to allow arterial blood sampling every 10–60 minutes throughout the entire procedure). Blood gases, pH, K+ and hematocrit were measured in each sample, and in some cases, electrolytes, and enzymes as well. The catheter was attached to a pressure transducer. The transducer was connected to a computer to monitor central arterial pressure (CAP). Other temperature and pressure parameters were also measured on-line by the same computer.

A 6F NIH catheter was inserted into a distal branch of the left brachial vein to allow computerized monitoring of central venous pressure (CVP). A thoracotomy was performed, and a 6 F coronary catheter was inserted into the left atrium to monitor left atrial pressure.

A 10 F arterial cannula was placed in the left femoral artery and a 16 F venous cannula was placed in the left femoral vein. Methyl prednisolone (80 mg) was introduced i.v. An esophageal tube was inserted, and 3 ml of Maalox was administered. The esophageal tube was fitted with a thermistor probe for recording deep esophageal temperature.

Due to the extensive surgical procedures, the baboon spent about five hours on anesthetic. After the EKG leads were in place, the animal was put in a netted sling and lowered into an insulated ice chest. It was then immersed in crushed ice. After 1 hour and 6 minutes of chilling in crushed ice, body temperature sank to 23° C. Nipride (25 mg sodium nitroprusside in 500 ml of 5% aqueous dextrose) infusion was begun at a rate of 6 ml/hr. The animal was placed on bypass 17 minutes later, when the temperature had declined to 21° C.

At that time, 200 ml of whole blood were removed from the baboon as venous effluent. The clamps were released which isolated the monkey's circulation from the bypass circuit, and 2 liters of solution A, to which were added 2 ml of 2M KCl (final concentration 2 mM KCL), were allowed to blood-substitute the animal. Following this, its heart was arrested by the i.v. administration of is ml of 2M KCl.

A blood-blood-substitute mixture was continuously removed as a venous effluent until 4 liters of solution A (to which 22 ml of 2M KCl had been added) replaced the circulating solution. After 50 minutes of chilled blood substitution, the primate's temperature had declined to 3° C. Flow through the animal appeared good, and there was little tendency for the pulmonary arterial wedge pressure to elevate along with perfusion of the femoral artery. The cause of this increased flow, and relatively rapid pace of temperature decline, may be related to the use of nitroprusside, and also the relatively sparing use of anesthetics during chilling, which resulted in the animal being somewhat more active as it was cooled.

Following blood-substitution, the animal was placed on circulatory standstill for one hour and 40 minutes. At the end of the standstill period, 2 liters of ice-cold solution A was added to the circuit, replacing 2 liters removed as venous effluent. The minimum body temperature recorded was 2.8° C. Rewarming was then begun. After 13 minutes of warming, the animal's body temperature reached 10° C., and 800 ml of a 1:3 mixture of blood and blood-substitute, followed by 450 ml of a 1:1 mixture, and finally, approximately 1 liter of whole blood was added to the circuit, replacing solution A.

Immediately after blood was introduced into the animal, heartbeat was detected. Over the next hour and 22 minutes, 40 ml of $NaHCO_3$, were introduced i.v. Mechanical ventilation was begun, and a dopamine drip (200 mg in 250 ml) was administered at 30 ml/hr. $CaCl_2$ (50 mg) was also injected i.v. Approximately one hour later, when the body temperature climbed to near normal, the animal was taken off bypass and placed on a whole blood drip. The animal's blood gases and blood pressures stabilized in the normal range.

One hour later, the cannulas were removed. Since the animal had been catheterized following a thoracotomy, it was decided that the long term post surgical management of the animal would not be attempted, due to the behavioral problems of restraining an untamed baboon while treating potential chest infections. When ventilation was discontinued after another hour, the animal displayed agonal movements and went into cardiac arrest. As the monkey's blood pressures and blood gases had stabilized, it is clear that the animal had the potential to survive after being blood-substituted below 10° C. (deep esophageal temperature) for 2 hours and 30 minutes.

EXAMPLE 9

Use of Solution A Without Augmentation in Blood Substitution of Primates

In this example an 8 kg juvenile male baboon of the species *Patio anubis* was chilled and blood-substituted below 10° C. for 1 hour and 22 minutes. Prior to chilling and blood replacement, a 4 F 60 cm Swan-Ganz arrow wedge catheter was placed in the pulmonary artery via the right femoral vein. This permitted measurement of the pulmonary arterial wedge pressure without performing a thoracotomy.

Keeping the animal anesthetically light, and using nitroprusside when the temperature fell to 28° C., improved flow through the bypass circuit. Although the entire procedure went smoothly, an i.v. injection of 50 mg calcium chloride after citrated blood was introduced during warming caused massive clot formation and termination of the experiment. At that time there was no heparin in the cardiovascular system.

Procedure.

The baboon was injected i.m. with 70 mg of ketamine. A 22 gauge×1-¼ in. catheter was inserted in the left cephalic vein, and 3 ml of 2.5% pentothal was injected i.v. The ape was then fitted with an endotracheal tube and moved to the x-ray room. It was placed on an x-ray table, and ventilated with a 1% mixture of isofluorane (Flether) in 100% $)_2$, and a 4 F 60 cm arrow wedge catheter was implanted in the pulmonary artery through the right femoral vein.

The ventilator was set at 20 bpm, its stroke volume was 200 ml, and the inspiratory/expiratory ratio was 37%. Airway pressure was maintained at approximately 10 mm Hg, and the volume delivered with each respiration was checked by examining the airway pressure trace on a CRT or strip-chart recorder. Airway pressure was monitored on-line by computer.

The animal was shaved, and a 1–3 ml/minute Ringer's lactate drip was initiated i.v., with its rate titrated to the animal's arterial blood pressure.

The extracorporeal circuit was as described in the previous Example. The oxygenator reservoir and circuit was filled with 2 liters of solution A.

A 20 gauge hydromere catheter was placed in the right femoral vein to allow computerized monitoring of central venous pressure (CVP). A 3-way stopcock was placed in-line to allow sampling. A 20 gauge hydromere catheter for monitoring arterial pressure was introduced into the right brachial artery. To it was attached a 3-way stop-cock (to allow arterial blood sampling every 10–60 minutes throughout the entire procedure). Blood gases, pH, K+ and hematocrit were measured in each sample, and in some cases, electrolytes, and enzymes as well. The catheter was attached to a pressure transducer. The transducer was connected to a computer to monitor central arterial pressure (CAP). Other temperature and pressure parameters were also measured on-line by the same computer.

A 14 F venous cannula was placed in the left femoral vein, and a 10 F arterial cannula was placed in the left femoral artery. After the venous cannula was implanted, 2.6 ml of heparin was injected i.v. An esophageal tube was inserted, and 3 ml of Maalox was administered. The esophageal tube was fitted with a thermistor probe for recording deep esophageal temperature. Methyl prednisolone (80 mg) was introduced i.v. The eyes were coated with lacrylube for protection. As the animal was anesthetically light, 1 ml of pentothal was administered i.v.

The EKG leads were in place, the animal was put in a netted sling and lowered into an insulated ice chest. It was then immersed in crushed ice. After 29 minutes of chilling in crushed ice, body temperature sank to 28° C. The animal was kept anesthetically light, Flether being turned off as the temperature dropped below 30° C. Nipride (sodium nitroprusside—25 mg in 500 ml of 5% aqueous dextrose) infusion was begun at a rate of 20 ml/hr and then increased to 40 ml/hr. Over the next 20 minutes, the Nipride drip was turned on and off sporadically, as the blood pressure and temperature fell. It was finally turned off when the animal was placed on bypass 27 minutes later and the temperature had declined to 23° C. At that time, the clamps were released which isolated the ape's circulation from the bypass circuit, 2 liters of solution A were allowed to blood-substitute the animal, and whole and diluted blood were removed as venous effluent, and saved for revival. Following this, its heart was arrested by the i.v. administration of 10 ml of 2M KCl.

A blood-blood-substitute mixture was continuously removed as a venous effluent until 4 liters of solution A replaced the circulating solution. After 39 minutes of chilled blood substitution, the primate's temperature had declined below 4° C. Flow through the animal was rapid. The pressure in the pulmonary circulation, which was readily measured, indicated that the circulation was good, and that the wedge pressure catheter was well placed.

After 50 minutes of blood-substitution below 10° C, the minimum body temperature recorded was 2.9° C. Rewarming was then begun, and after 28 minutes of warming, the animal's body temperature reached 10° C., and 750 ml of whole blood were added to the circuit, replacing solution A.

Heartbeat was detected 8 minutes after blood was re-infused into the animal. Over the next 30 minutes while the animal warmed, 10 ml of $NaHCO_3$, were introduced i.v. and $CaCl_2$ (50 mg) was also injected i.v.$_1$ as was 80 mg of methyl prednisolone. Within a few minutes of adding the $CaCl_2$, massive clot formation was evident. It was thought that the blood, which was anti-coagulated with citrate, clotted as a result of adding $CaCl_2$. The Experiment was then discontinued.

In this experiment, the rate of flow of blood substitute through the animal and bypass circuit appeared high, while the left atrial pressure remained acceptably low. The factors which were thought to contribute to this result were the use of nitroprusside, and the maintenance of a light anesthetic state during the cooling process. 1–2 ml of heparin will be added to the blood prior to its re-introduction into the animal. It is believed that heparinizing the re-introduced blood will eliminate the massive clotting which caused an unexpected end to this experiment.

EXAMPLE 10
Ice-Cold Blood Substitution of a Dog with Solution HLB.

Place a 25–30 Kg dog on partial cardio-pulmonary bypass. Surface and core cool the dog to near the ice point (1–3° C.). Replace the dog's blood with solution HLB hypothermic blood substitute, described in Example 1. Retain the blood for transfusion during rewarming. Reduce the animal's body temperature to near the ice point (below 4° C.) and then rewarm. Replace the blood substitute with blood with warming and revive the animal.

Preparation.

Catheterize the dog by means of the right radial vein, injected iv with pentothal, then fit with an endotracheal tube and ventilate with isofluorane (or Flether) in 100% $O_2$. Initiate a Ringer's lactate drip at a rate titrated to the dog's arterial blood pressure (approx. 40 ml/hr iv). Place the dog on a cooling blanket cooled with recirculating ice water. Catheterize the right carotid artery to allow for blood pressure (CAP) monitoring, and add a 3-way stopcock in-line to allow arterial blood sampling every 10–60 min. throughout the entire procedure. Insert a foley catheter for urine collection and measure the urine volume throughout the procedure. Implant a 2 lumen, 7 F, Swan Ganz wedge catheter via the right jugular vein or right femoral vein, which is fed through the right heart into the pulmonary artery. Use the distal port to measure pulmonary wedge pressure (PAW), the proximal port is used for central venous pressure (CVP). (If necessary CVP may be measured with a catheter inserted in one of the brachial veins.) Isolate the left femoral artery and vein and prepare for cannulation. Heparinize the animal (approx. 5000 u). Insert a Biomedicus venous return cannula (15–19 F) in the femoral vein and a Biomedicus arterial cannula (12–15 F) in the femoral artery. Measure the activated clotting time (ACT) every 45 min. (until blood substitution) and adjust the heparin such that it remains greater than 400 sec. Attach a thermocouple approx. midway to an esophageal tube and insert the unit so that the tube enters the stomach. A second thermocouple is placed rectally. Attach ECG leads. Add Solu-Delta-Cortef (Upjohn, veterinary prednisolone Na succinate), 80 mg by iv injection. Coat the eyes with Terrimycin (or Lacrylube), and add DiGel (or Maalox, 20 ml) through the esophageal tube.

Measurements.

Measure arterial blood gasses, pH and hematocrit in every blood sample, and in some cases electrolytes, enzymes and other chemistries. Monitor esophageal and rectal temperature as well as the arterial inflow and venous return blood temperatures. Monitor CAP, PAW, CVP, ECG, and airway pressure. Temperatures should be displayed digitally and stored as a function of time in a computerized data acquisition system. The pressures and ECG should be displayed as real time waveforms or as numerical data and stored by the computer.

Bypass Circuit Components.

The circuit features a Biomedicus centrifugal blood pump and flow meter, a Terumo hollow fiber membrane oxygenator with built-in heat exchanger, Shiley hard shell venous reservoir with filter and a secondary heat exchanger with integral bubble trap (Electromedics) located as close to the animal as possible. A drain segment is located near the inlet of the venous reservoir and terminates with a check valve. This allows rapid and efficient blood/blood-substitute exchanges. There is an A-V shunt segment that allows circulation when not on bypass.

The venous reservoir can be filled from either the 1 liter separatory funnel through the "quick prime" port or from dual infusion bags through one of the cardiotomy ports. The arterial line from the oxygenator to the arterial cannula and the A-V shunt are constructed from ¼" tubing; the venous return, drain and pump-head lines are ⅜". In those segments where severe bending can occur, heavy-wall tubing is used or the tube is braced with "spiral wrap."

The patient loop is double wrapped and the entire circuit (sans the factory sterilized reservoir, secondary heat exchanger and oxygenator) is ethylene oxide gas sterilized as six basic sections (pump-head, flow meter section, central bypass loop, funnel, infusion line, and gas filter line).

Bypass Circuit Support.

Ice water, pumped from one of two 10 gal. insulated reservoirs, is used to cool the oxygenator and secondary heat exchangers. The other reservoir supplies the cooling blanket. At the onset of surgery, ice water is circulated through the cooling blanket. At the onset of bypass, room temp. water is circulated through the circuit heat exchangers.

Temperature is slowly decreased by adding ice to is the reservoir, in quantities sufficient to maintain a 7–10° C. difference between the esophageal and blood stream temperatures. After blood substitution (i.e. to a hematocrit of less than about 4%) full ice water flow is commenced.

Upon rewarming, ice is removed from the reservoir and the heater is activated. The temperature of the warming stream is limited to a maximum of 10° C. greater than the venous return temperature, by manual adjustment of the heater thermostat.

The oxygenator is supplied with sterile, filtered 100% $O_2$.

Blood Substitution.

The circuit is primed with 2 liters of solution L (Example 1), and recirculated through the A-V shunt to ensure temperature-gas equilibrium. The cannulas are attached to the arterial and venous lines of the bypass circuit, and the lines remain clamped. The cooling blanket is wrapped around the patient who is surface cooled until a deep esophageal temperature of 35° C. is reached.

The clamps are removed, and bypass is commenced with the solution L-diluted blood stream at room temperature (approx. 25° C.). At the onset of cooling, gaseous anesthesia is discontinued, and the dog is managed with 2.5% pentothal.

The blood stream is gradually cooled until the animal has an esophageal temperature of 20° C., at which time blood is removed by clamping the venous return at the reservoir inlet and draining from the drain segment while L solution is infused. During this exchange, an additional 2 liters of L solution is added to the venous reservoir and when the level of L solution drops to 250 ml, approximately 6 liters of HLB is added stepwise until all of the blood is removed (HCT less than 2%, visual observation). Approximately 4 liters of blood/blood-substitute mixtures collected in sterile bottles and retained for reinfusion. The very dilute blood mixture (about 5 ½ liters) is discarded.

After 4 liters have been exchanged (i.e. after the addition of 2 liters of solution L and 2 liters of solution HLB), 20 meq KCl will be injected via a stopcock on the secondary heat exchanger, to arrest the heart. During the exchange, the inflow is adjusted such that the PAW is kept below 5 mm Hg and the rate of efflux equals the rate of influx, i.e. as close to isovolemia as possible. At the end of the exchange the final reservoir level will be about 500 ml, the PAW below 5 mm Hg and the CVP less than 5 mm Hg. Flow will be adjusted such that isovolemia will be maintained (constant reservoir level and the above pressure levels, i.e. PAW <5 mm Hg and CVP <5 mm Hg).

When almost all of the blood is removed (HCT less than 4%, visual observation), the cooling stream can be reduced to ice water temperature (filling the reservoir with ice), and the dog rapidly cooled to its minimum temperature. If the HCT is observed to rise at any time during cold perfusion, the blood mixture can be removed by exchanging with 2 to 4 liters of solution HLB by the method described above.

During the entire procedure, arterial blood samples are taken and blood gasses, pH, HCT, and in some cases electrolytes, and other blood chemistries monitored.

After about 1–2 hours of blood substituted cooling, the dog's temperature will be about 1–4° C., and rewarming will begin. The dog will be rewarmed, by removing the ice from the supply reservoir and warming its contents with the heater which in turn warms the blankets. When the esophageal temp reaches 15° C., 4 liters of solution L with 25 g mannitol will be exchanged with the solution HLB followed by the 4 liters of collected blood mixture. The effluent will be discarded.

The animal will be warmed gently, blood stream temperature differential less than 10° C. and never above 40° C. The heart will spontaneously begin to beat. When the animal's temperatures (esophageal and rectal) reach about 35° C., physiological parameters are stabilized, and it can support itself, it can be weaned from the extracorporeal circuit.

EXAMPLE 11

Reviving An Ice-Cold Blood-Substituted Dog.

A 26.8 kg male dog was anesthetized with nembutal and intubated. It was moved to the operating room, ventilated, and catheterized with venous, Foley, arterial, and Swan-Ganz catheters, and after i.v. heparin, its right femoral artery and vein were cannulated. An esophageal tube was inserted and antacid administered. Temperature sensors were placed in the esophagus and the rectum. Methyl prednisolone was injected i.v.

The animal was wrapped in a cooling blanket, and surface cooling initiated. The animal's cannulas were connected to a bypass circuit, which consisted of a vortex blood pump, an oxygenator with a built-in heat exchanger, a secondary in-line heat exchanger, and a funnel for the rapid administration of blood and blood substitute. Whole blood (225 ml) was removed from the dog and saved for rewarming. Blood volume was quickly replaced with HLB solution. The bypass circuit containing 1.05 liters of HLB solution was opened to the animal, and core cooling began.

Thirty three liters of blood substitute were exchanged. By the time the ice-point was approached, the hematocrit was far below 1%. The animal's deep esophageal temperature was below 10° C. for 4 hours and 5 minutes, with a minimum recorded temperature of 0.7° C. (Table 2).

Following the hypothermic period, the animal was warmed. When body temperature climbed past 10° C., venous effluent and whole blood previously collected, as well as a donor blood, was returned to the circuit; hematocrit increased with increasing temperature. Lidocaine and bicarbonate were administered, the heart defribillated, an ventilation begun. When blood pressure and body temperatures approached normal, the animal was weaned from bypass, and protamine and Lasix injected. Several hours after warm-up, the animal was conscious and responsive. The animal remained alive and well after the procedure.

EXAMPLE 12

Reviving an Ice-Cold Blood-Substituted Baboon.

A 24 kg male baboon of the species *Papio annubis* was anesthetized first with ketamine and acepromazine i.m., then with i.v. pentothal. It was then immobilized with pancuronium bromide. It was intubated, ventilated, and catheterized with venous, Foley, and arterial catheters. The animal was wrapped in a cooling blanket, and surface cooling initiated. After i.v. heparin was administered, the baboon's right femoral artery and bilateral femoral veins were cannulated. Temperature sensors were placed in the esophagus, rectum and brain. The animal was instrumented for EKG, somatosensory evoked potentials (SSEPs) and EEG. Dexamethazone was injected i.v.

The animal's cannulas were connected to a bypass circuit, which consisted of a vortex blood pump, an oxygenator with a built-in heat exchanger, and a funnel for the rapid administration of blood and blood substitute. Whole blood (300 ml) was removed from the baboon and saved for rewarming. The volume was quickly replaced with 300 ml of physiological saline solution. The bypass circuit, containing 2 liters of Plasmalyte (commercially available electrolyte solution), was opened to the animal and core cooling begun.

After the deep esophageal temperature declined below 13° C., another 2 liters of Plasmalyte containing 12.5 g of mannitol, was added to the circuit, replacing the mixture of blood and Plasmalyte which previously filled the circuit. This diluted blood was saved for use during warming. Immediately afterwards, 10 liters of HLB solution were added, replacing the Plasmalyte. By the time the ice-point was reached, the hematocrit was far below it. When the animal reached brain temperature of 3.4° C. and deep esophageal temperature of 2.8° C., the blood pump was stopped and the animal was maintained under a condition of circulatory arrest (standstill) for 45 minutes. After this period, circulation was resumed.

Following the hypothermic period, 4.2 liters of HLB solution were added to the bypass circuit, and the animal warmed. When body temperature reached 15° C., 2 liters of Plasmalyte were added to the circuit to replace the HLB solution. Mannitol (6.25 g/l) was added to the Plasmalyte in the circuit. Additionally, venous effluent and whole blood previously collected, as well as donor blood cells and fresh-frozen plasma, were returned to the circuit; the animal's hematocrit increased with increasing body temperature. Another 12.5 g of mannitol were added to the circuit. When the esophageal and rectal temperatures approached normal, the heart fibrillated during warming and began beating. Ventilation was begun. When blood pressure and body temperatures approached normal, the animal was injected with protamine i.v., weaned from bypass, its cannulas and catheters removed, and its incisions closed.

The animal's deep esophageal temperature had been below 15° C. for 3 hours, and below 10° C. for 2 hours 17 minutes, with a minimum recorded temperature of 2.8° C. (Table 3). The following morning, the animal was able to sit erect in its cage and pick up and eat pieces of banana, as well as drink apple juice. It remained alive and well until sacrificed more than one week later for histological evaluation.

TABLE 2

REVIVAL OF AN ICE-COLD BLOOD-SUBSTITUTED DOG.

| TIME | SOLUTION | TE °C. | TR °C. | MAP mmHg | HR bpm | PAW mmHg | CVP mmHg | Flow L/min | pH | PCO$_2$ | PO$_2$ | Na | K | Hct |
|---|---|---|---|---|---|---|---|---|---|---|---|---|---|---|
| 11:57 am | | | 36.1 | | | | | | | | | | | |
| 12:21 pm | 225 ml HLB in & 225 ml blood out @12:19 pm | | 35.2 | 129 | 133 | 12 | 3 | | | | | | | |
| 12:39 pm | | 32.6 | 34.8 | 134 | 141 | 12 | 3 | | | | | | | |
| 12:40 pm | | | | | | | | | 7.52 | 25.1 | 403 | 144 | 2.7 | 34 |
| 12:52 pm | | | | | | | | | 7.41 | 34.7 | 581 | 141 | 3.1 | 37 |
| 1:35 pm | @1:36 pm on bypass w/1.05 L HLB | 32.2 | 32.9 | 141 | 132 | 12 | 5 | 1.7 | | | | | | |
| 1:40 pm | | 29.9 | 31.5 | 115 | 128 | 10 | 3 | 1.7 | | | | | | |
| 1:43 pm | | 26.7 | 29.7 | 105 | 122 | 8 | 3 | 1.8 | | | | | | |
| 1:46 pm | | | | | | | | | 7.36 | 37.1 | 719 | 143 | 2.6 | 24 |
| 1:50 pm | 5 L HLB | 21.9 | 24.8 | 66 | 77 | 7 | 2 | 0.9 | | | | | | 0 |
| 1:58 pm | 4 L HLB | 18.5 | 20.1 | 19 | | | | 1.1 | | | | | | |
| 2:00 pm | 4 L HLB | 14.9 | 18.8 | 28 | | | | 1.0 | 7.48 | 9.2 | 812 | 155 | 2.5 | 0 |
| 2:02 pm | | | | | | | | | 7.50 | 8.8 | 999+ | 165 | 3.6 | 0 |
| 2:04 pm | | 10.4 | 16.9 | 37 | | | | 1.5 | | | | | | |
| 2:05 pm | | 9.9 | 16.2 | 37 | | | | | | | | | | |
| 2:08 pm | 4 L HLB | 8.6 | 15.3 | 37 | | | | 1.5 | | | | | | |
| 2:14 pm | | | | | | | | | 7.50 | 11.6 | 999+ | 159 | 4.2 | |
| 2:16 pm | 2 L HLB | 5.7 | 12.3 | 27 | | | | 1.5 | | | | | | |
| 2:20 pm | | | | | | | | | 7.50 | 13.7 | 999+ | 151 | 5.1 | |
| 2:22 pm | | 3.7 | 10.4 | 36 | | | | 1.4 | | | | | | |
| 2:25 pm | | 3.3 | 9.8 | 35 | | | | 1.6 | | | | | | |
| 2:27 pm | | 2.9 | 9.1 | 36 | | 1 | | 1.4 | | | | | | |
| 2:33 pm | | 2.1 | 7.4 | 37 | | | | 1.4 | | | | | | |
| 2:44 pm | 2 L HLB | | | | | | | | 7.54 | 11.6 | 999+ | 150 | 4.6 | |
| 2:47 pm | | 1.4 | 4.8 | 36 | | 3 | 1 | 1.3 | | | | | | |
| 2:50 pm | | 1.2 | 4.3 | 37 | | 3 | 1 | 1.3 | | | | | | |
| 2:52 pm | | 1.2 | 4.2 | 37 | | 3 | 1 | 1.3 | | | | | | |
| 2:59 pm | 2 L HLB | 1.1 | 3.4 | 21 | | | | 0.6 | | | | | | |
| 3:55 pm | | 0.9 | 2.3 | 22 | | | | 0.4 | | | | | | |
| 4:00 pm | | | | | | | | | 7.63 | 9.6 | 999+ | 150 | 5.4 | |
| 4:22 pm | 3 L HLB | 1.1 | 2.1 | 20 | | | | 0.3 | | | | | | |
| 5:00 pm | 2 L HLB | 0.8 | 1.6 | 18 | | | | 0.4 | | | | | | |
| 5:30 pm | 3 L HLB | 0.8 | | | | | | | | | | | | |
| 5:50 pm | | | | | | | | | 7.48 | 11.0 | 999+ | 150 | 5.7 | |
| 5:56 pm | | 1.8 | 1.8 | 19 | | | | 0.4 | | | | | | |
| 6:04 pm | | 4.7 | 2.8 | 27 | | | | 1.0 | | | | | | |
| 6:06 pm | 2 L HLB | 6.6 | 3.3 | 27 | | | | 1.1 | | | | | | 0 |
| 6:08 pm | 2 L Half blood | 9.7 | 4.1 | 30 | | | | 1.1 | | | | | | 20 |
| 6:09 pm | | 9.9 | 4.2 | | | | | | | | | | | |
| 6:11 pm | | 10.7 | 5.3 | 31 | 18 | 7 | | 1.0 | | | | | | |
| 6:12 pm | | | | | | | | | 7.30 | 28.0 | 902 | 151 | 4.6 | 26 |
| 6:15 pm | | 13.8 | 6.7 | 30 | 24 | 13 | 2 | 1.1 | | | | | | |
| 6:25 pm | | 20.2 | 10.7 | 38 | | 6 | 1 | 1.4 | 7.28 | 27.2 | 716 | 154 | 5.0 | 27 |
| 6:34 pm | 1 L blood | | | | | | | | | | | | | |
| 6:39 pm | | | | | | | | | 7.34 | 38.9 | 670 | 158 | 3.2 | 26 |
| 6:42 pm | | 29.2 | 18.1 | 60 | 143 | 15 | 2 | 1.7 | | | | | | |
| 6:48 pm | | | | | | | | | 7.37 | 28.9 | 587 | 154 | 2.9 | 27 |
| 6:57 pm | | 32.8 | 32.2 | 132 | 161 | 8 | 0 | 1.6 | | | | | | |
| 7:00 pm | | | | | | | | | 7.33 | 27.3 | 496 | 150 | 2.7 | |

Te: Esophageal Temperature; Tr: Rectal Temperature; MAP: Mean Arterial Pressure; HR: Heart Rate; PAW: Pulmonary Arterial Wedge pressure; CVP: Central Venous Pressure

TABLE 3

REVIVAL OF ICE--COLD BLOOD--SUBSTITUTED BABOON.

| TIME | TE °C. | TR °C. | TB °C. | MAP mmHg | HR bpm | ICP mmHg | Flow L/min | pH | PCO$_2$ | PO$_2$ | HLB | Plas-malyte+ | Blood | Hct |
|---|---|---|---|---|---|---|---|---|---|---|---|---|---|---|
| 1:23 pm | | | | | | | | | | | | 1.6 L + 12.5 g mannitol | (on bypass) | ≅18 |
| 1:27 pm | 31.3 | 32.8 | 33.2 | 60 | 83 | 9 | 2.2 | | | | | | | |
| 1:30 pm | 28.5 | 31.1 | 32.5 | 60 | 67 | 9 | 2.1 | | | | | | | |
| 1:32 pm | 23.4 | 29.0 | 30.9 | 50 | 45 | 8 | 2.2 | | | | | | | |
| 1:35 pm | 19.3 | 26.6 | 28.0 | 50 | 27 | 9 | 2.1 | | | | | | | |
| 1:37 pm | 18.0 | 25.5 | 26.5 | 50 | 24 | 11 | 2.2 | | | | | | | |
| 1:38 pm | 17.6 | 24.7 | 25.6 | 50 | 23 | 9 | 2.0 | | | | | | | |
| 1.40 pm | 16.8 | 23.7 | 24.3 | 50 | 25 | 8 | 2.0 | | | | | | | |
| 1:44 pm | 18.1 | 22.8 | 23.1 | 50 | 22 | 10 | 2.0 | | | | | | | |
| 1:46 pm | 18.0 | 22.2 | 22.3 | 50 | | 8 | 2.1 | | | | | 0.3 L | | |
| 1:50 pm | | | | | | | | | | | | 0.1 L | | |
| 1:55 pm | 12.2 | 19.3 | 18.2 | 50 | | 4 | | | | | 7 L | | | 0 |
| 2:02 pm | 11.7 | 18.0 | 16.1 | 50 | | 15 | 1.2 | 7.40 | 27 | 530 | 2 L | | | |
| 2:05 pm | 12.7 | 17.5 | 15.1 | 40 | | 9 | 1.0 | | | | 3 L | | | |
| 2:10 pm | 11.3 | 16.9 | 14.1 | 40 | | 9 | 1.3 | | | | | | | |
| 2:14 pm | 10.5 | 16.2 | 13.3 | 50 | | 11 | 1.3 | 7.34 | 17.1 | 578.6 | | | | |
| 2:21 pm | 9.6 | 15.0 | 11.9 | 50 | | 11 | 1.3 | | | | | | | |
| 2:25 pm | 8.8 | 14.3 | 11.0 | 50 | | 10 | 1.3 | | | | | | | |
| 2:30 pm | 7.9 | 13.4 | 9.9 | 50 | | 10 | 1.3 | 7.37 | 21.2 | 782 | | | | |
| 2:40 pm | 6.4 | 11.7 | 8.0 | 50 | | 9 | 1.3 | | | | | | | |
| 2:49 pm | 5.3 | 10.4 | 6.7 | 55 | | 10 | 1.2 | | | | | | | |
| 2:54 pm | 5.4 | 9.8 | 6.3 | 50 | | 7 | 1.2 | | | | | | | |
| 3:18 pm | 3.9 | 8.6 | 4.6 | 50 | | 7 | 1.0 | | | | | | | |
| 3:29 pm | 3.2 | 7.8 | 3.8 | 50 | | 8 | 1.0 | | | | | | | |
| 3:32 pm | 3.0 | 7.6 | 3.6 | 55 | | 8 | 1.0 | | | | | | | |
| 3:35 pm | 2.9 | 7.4 | 3.5 | 50 | | 7 | 1.0 | | | | | | | |
| 3:37 pm | 2.8 | 7.3 | 3.4 | | | 3 | | | | | | | | |
| 4:22 pm | 3.7 | 10.1 | 4.8 | | | 1 | | | | | | | | |
| 4:24 pm | 4.3 | 10.2 | 4.9 | 45 | | 6 | 1.7 | | | | | | | |
| 4:27 pm | 6.5 | 10.4 | 6.4 | 55 | | 8 | 1.0 | | | | | 2.2 L | | |
| 4:32 pm | 8.3 | 10.5 | 7.7 | 60 | | 8 | 1.1 | | | | | 3 L | | |
| 4:34 pm | 9.0 | 10.6 | 8.5 | 65 | | 10 | 1.0 | | | | | | | |
| 4:36 pm | 9.4 | 10.8 | 9.0 | 65 | | 7 | 1.0 | | | | | | | |
| 4:38 pm | 9.9 | 10.9 | 9.4 | 60 | | 6 | 1.0 | | | | | | | |
| 4:39 pm | 10.0 | 10.9 | 9.6 | 60 | | 7 | 1.0 | | | | | | | |
| 4:45 pm | 11.4 | 11.4 | 11.2 | 75 | | 10 | 1.0 | | | | | | | |
| 4:47 pm | 11.9 | 11.6 | 11.9 | 80 | | 9 | 1.0 | | | | | | | |
| 4:51 pm | 13.2 | 12.2 | 13.5 | 85 | | 7 | 0.9 | | | | | | | |
| 4:53 pm | 14.1 | 12.6 | 14.6 | 85 | slow | 7 | 0.8 | 7.37 | 14 | 762 | | | | |
| 4:55 pm | 14.6 | 15.2 | 15.9 | 90 | slow | 6 | | | | | | 2 L | 0.3 L | 0 |
| 4:59 pm | | | | | | | | | | | | | 1/10 blood 2 L 1/4 blood/ 0.3 L plasma | |
| 5:01 pm | | | | | | | | | | | | | | |
| 5:05 pm | 18.0 | 15.3 | 18.1 | 55 | | | | 7.33 | 22 | 224 | | | | 2 |
| 5:16 pm | | | | | | | | | | | | | +12.5 g mannitol | |
| 5:20 pm | 24.6 | 20.0 | 24.5 | 44 | fib | 12 | 2.1 | | | | | | | |
| 5:24 pm | | | | | | | | | | | | | 0.3 L plasma | |
| 5:25 pm | 25.0 | 20.9 | 25.2 | 44 | fib | 13 | 2.0 | 7.30 | 25.3 | 593 | | | | |
| 5:36 pm | | | | | | | | | | | | | 0.4 L blood + 12.5 g mannitol | 12 |
| 5:37 pm | 26.7 | 22.4 | 28.7 | 45 | fib | 12 | 2.0 | | | | | | | |
| 5:43 pm | | | | | | | | | | | | | 0.3 L blood | |
| 5:55 pm | 32.0 | 24.8 | 32.8 | 45 | fib | 10 | 2.2 | | | | | | | |
| 5:57 pm | 32.2 | 25.3 | 32.9 | 45 | fib | 8 | 2.2 | | | | | | | |
| 6:10 pm | 35.3 | 28.8 | 36.6 | 55 | beat | 11 | | | | | | | | |
| 6:13 pm | 36.3 | 30.3 | 36.8 | | ? | | | | | | | | | |
| 6:23 pm | 37.3 | 33.7 | 36.2 | 50 | ? | 7 | 1.3 | 7.34 | 28.2 | 435 | | | | 17 |

TABLE 3-continued

REVIVAL OF ICE--COLD BLOOD--SUBSTITUTED BABOON.

| TIME | TE ° C. | TR ° C. | TB ° C. | MAP mmHg | HR bpm | ICP mmHg | Flow L/min | pH | $PCO_2$ | $PO_2$ | HLB | Plas-malyte+ | Blood | Hct |
|---|---|---|---|---|---|---|---|---|---|---|---|---|---|---|
| 6:34 pm | | | | | | | | 7.39 | 31.9 | 322 | | | | 20 |
| 6:36 pm | | | | | | | | | | | | | 0.3 L plasma | |

Te: Esophageal Temperature; Tr: Rectal Temperature; Tb: Brain Temperature; MAP: Mean Arterial Pressure; HR: Heart Rate; ICP: Intra-Cranial Pressure The invention described above and claimed herein below embodies novel solutions that may be useful in a number of procedures. Those ordinarily skilled in the art may be capable in light of the teaching of the specification and claims to make certain additions or modifications to the invention without departing from the essence of the invention disclosed.

What is claimed is:

1. A method of making a terminally heat sterilized plasma like solution, said method comprising:
   (a) providing a solution comprising:
      a starch having a molecular weight of at least 150,000 daltons;
      $Na^+$ present in a concentration ranging from 70 mM to about 160 mM;
      $Ca^+$ present in a concentration ranging from about 0.5 mM to 4.0 mM;
      $Cl^-$ present in a concentration ranging from 70 mM to 160 mM;
      $Mg^+$ present in a concentration ranging from 0 mM to 10 mM;
      $K^+$ present in a concentration ranging from 0 mM to 5 mM,
      an organic carboxylic acid, salt or ester thereof; and
      a simple sugar,
      wherein said solution does not include a conventional biological buffer, and
   (b) heating said solution to a temperature and for a period of time sufficient to produce a terminally heat sterilized plasma like solution.

2. The method of claim 1, wherein said method further comprises a step of adding bicarbonate to said terminally heat sterilized plasma like solution following said heating step.

3. The method according to claim 1, wherein said heating is under pressure.

4. The method according to claim 1, wherein said heating is to a temperature above the boiling point of water.

5. The method according to claim 1, wherein said heating is by autoclaving.

* * * * *